US008673967B2

(12) United States Patent
Bhaggan et al.

(10) Patent No.: US 8,673,967 B2
(45) Date of Patent: Mar. 18, 2014

(54) PROCESS

(75) Inventors: Krishnadath Bhaggan, Wormerveer (NL); John B. Harris, Wormerveer (NL); Miriam Van Wanroij, Wormerveer (NL)

(73) Assignee: Loders Croklaan B.V., Wormerveer (NL)

( * ) Notice: Subject to any disclaimer, the term of this patent is extended or adjusted under 35 U.S.C. 154(b) by 505 days.

(21) Appl. No.: 12/601,287

(22) PCT Filed: May 27, 2008

(86) PCT No.: PCT/GB2008/001801
§ 371 (c)(1),
(2), (4) Date: Jun. 15, 2010

(87) PCT Pub. No.: WO2008/142433
PCT Pub. Date: Nov. 27, 2008

(65) Prior Publication Data
US 2010/0286258 A1    Nov. 11, 2010

(30) Foreign Application Priority Data

May 24, 2007 (EP) .................................... 07252128

(51) Int. Cl.
*A01N 43/16* (2006.01)
*C12P 17/06* (2006.01)
*A23D 9/013* (2006.01)
*B65D 81/00* (2006.01)
*A23D 7/00* (2006.01)

(52) U.S. Cl.
USPC ............. 514/458; 435/125; 426/531; 426/86; 426/601

(58) Field of Classification Search
USPC ............. 514/458; 435/125; 426/531, 86, 601
See application file for complete search history.

(56) References Cited

U.S. PATENT DOCUMENTS

| | | | |
|---|---|---|---|
| 2,349,270 A | 5/1944 | Hickman | |
| 2,349,789 A | 5/1944 | Hickman | |
| 4,971,660 A | 11/1990 | Rivers, Jr. | |
| 5,157,132 A | 10/1992 | Tan et al. | |
| 5,487,817 A | 1/1996 | Fizet | |
| 5,512,691 A | 4/1996 | Barnicki et al. | |
| 5,908,940 A | 6/1999 | Lane et al. | |
| 6,159,347 A | 12/2000 | Sumner, Jr. et al. | |
| 6,277,431 B1 | 8/2001 | Berry et al. | 426/601 |
| 6,399,138 B1* | 6/2002 | Cain et al. | 426/611 |
| 6,552,208 B1 | 4/2003 | Alander et al. | 554/208 |
| 6,660,491 B2 | 12/2003 | Norinobu et al. | |
| 6,759,543 B2 | 7/2004 | Bardet et al. | |
| 6,838,104 B2* | 1/2005 | Jacobs | 426/494 |
| 2003/0108650 A1 | 6/2003 | Kohler et al. | |
| 2003/0130532 A1 | 7/2003 | Bardet et al. | |
| 2003/0158429 A1 | 8/2003 | Albiez et al. | |
| 2004/0158083 A1 | 8/2004 | Choo et al. | |
| 2005/0033027 A1 | 2/2005 | Rohr et al. | |
| 2005/0054866 A1 | 3/2005 | Rohr et al. | |
| 2005/0101820 A1 | 5/2005 | May et al. | |
| 2005/0250953 A1 | 11/2005 | May et al. | |
| 2005/0255544 A1* | 11/2005 | Svendsen et al. | 435/69.1 |
| 2006/0088644 A1 | 4/2006 | Choo et al. | 426/601 |
| 2006/0106093 A1 | 5/2006 | Rich et al. | 514/458 |

FOREIGN PATENT DOCUMENTS

| | | | |
|---|---|---|---|
| DE | 102004041612 | 3/2005 | |
| EP | 0333472 | 9/1989 | |
| EP | 1044687 | 10/2000 | |
| EP | 1097985 | 5/2001 | |
| EP | 1746149 | 1/2007 | ............... C11B 3/12 |
| FR | 2 691 974 | 1/1993 | ............... C12P 7/02 |
| GB | 501194 | 2/1939 | |
| JP | 57-156482 | 9/1982 | .......... C07D 311/72 |
| WO | WO 00/15201 | 3/2000 | |
| WO | WO 01/51596 | 7/2001 | |
| WO | WO 01/70046 | 9/2001 | |
| WO | WO 03/102118 | 12/2003 | |
| WO | WO 2005/051294 | 6/2005 | |
| WO | WO 2005/066351 | 7/2005 | |

OTHER PUBLICATIONS

Wikepedia (2005) 1page.*
Australian Search Report and Written Opinion issued in Singapore Patent Application No. 200907699-3 (Nov. 3, 2010).
European Search Report issued in European Patent Application No. EP 07 25 2128 (Jan. 7, 2008).
Chu et al., "Factors affecting pre-concentration of tocopherols and tocotrienols from palm fatty acid distillate by lipase-catalysed hydrolysis", Food Chemistry, 97(1):55-59 (Oct. 2002).
Tan et al., "Valorisation of palm by-products as functional components", European Journal of Lipid Science and Technology, 109(4):380-393 (Apr. 2007).

(Continued)

*Primary Examiner* — Shirley V Gembeh
(74) *Attorney, Agent, or Firm* — Morgan, Lewis & Bockius LLP

(57) ABSTRACT

A process for producing a composition comprising at least 3% by weight of total tocopherols and tocotrienols comprises:

providing a product obtained from palm oil comprising tocopherols and tocotrienols, together with free fatty acids and monoglycerides and diglycerides of fatty acids;

hydrolysing at least part of the monoglycerides and diglycerides with a lipase to form the corresponding free fatty acids;

removing at least part of the free fatty acids after hydrolysis; and recovering a composition comprising a higher level of tocopherols and tocotrienols than are present in the product obtained from palm oil.

23 Claims, 3 Drawing Sheets

(56) References Cited

OTHER PUBLICATIONS

European Search Report issued in EP Application No. 07252128.9 (Jan. 7, 2008).
Black et al "Palm Tocotrienols Protect ApoE +/− Mice from Diet-Induced Atheroma Formation" Journal of Nutrition 130: 2420-2426 (2000).
Bornscheuer "Enzymes in Lipid Modification" Wiley-VCH, pp. 4 and 11-14 (2000).
Bornscheuer et al. "Hydrolases in Organic Synthesis: regio- and stereoselective biotransformations" Wiley-VCH, pp. 8, 9 and 13 (1999).
Carotech, Tocomin® 50%, Certificate of Analysis.
Rogalska et al. "Stereoselective hydrolysis of triglycerides by animal and microbial lipases" Chirality 5(1): 24-30 (1993) (Pubmed abstract).
Tocomin® 50% product sheet, 2008.
International Search Report issued in PCT application No. PCT/GB2008/001801 (Sep. 2008).

* cited by examiner

PROCESS

This application is a 371 filing of PCT/GB2008/001801 (WO 2008/142433), filed May 27, 2008, claiming priority benefit of European Patent Application No. 07252128.9, filed May 24, 2007.

This invention relates to a process for producing a composition comprising tocopherols and tocotrienols and to the compositions thereby produced.

Palm oil contains a number of valuable components and is produced on a large scale for use in a number of different applications, including in food. Palm oil is typically obtained from the flesh of the palm fruit (*Elaeis guineensis*). A palm tree normally produces approximately one fruit bunch, containing as many as 3,000 fruitlets, each month. Each palm tree normally continues producing fruit economically for up to 25 years. This ensures a good supply of palm oil. Palm oil is available in a variety of forms, including crude palm oil, refined palm oil and fractions thereof, such as palm olein and palm stearin.

Crude palm oil contains mainly triglycerides of fatty acids having 12 to 18 carbon atoms, with palmitic acid (C16) and oleic acid (C18:1) being the predominant acid residues. Generally, palm oil is refined and processed in order to use the glycerides and/or the fatty acids. Since crude palm oil contains smaller amounts of other components, it is generally refined in order to obtain a product that contains more of the triglycerides and less of the minor components, particularly those that impart odour or colour to the oil.

Crude palm oil is usually refined by steam distillation. In the steam distillation process, the palm oil, containing mainly triglycerides, is separated from free fatty acids (FFAs) (i.e., those acids that are not bound as glycerides) and other volatile compounds. The process can also decolourise the oil by decomposing and removing the compounds that are responsible for the colour of the oil. The volatile fraction that is obtained in this process is known as palm fatty acid distillate (PFAD).

Palm fatty acid distillate typically contains not only free fatty acids but also monoglycerides, diglycerides and other valuable materials including tocotrienols ($\alpha$-, $\beta$-, $\gamma$-, and $\delta$-), tocopherols ($\alpha$-, $\beta$-, $\gamma$-, and $\delta$-) sterols and squalene.

Processes are known for separating tocotrienols and tocopherols (sometimes collectively known as tocols) from palm oil products.

U.S. Pat. No. 6,838,104 relates to the production of tocotrienol compounds from biological sources, including palm oil. The process may involve a step of saponification using 50% sodium or potassium hydroxide. However, the resulting mixture after saponification contains soaps together with the tocols and requires that triglycerides are added before it can be purified by distillation. Also, a further step of solvent wintering is required.

WO 2005/066351 describes a method for reducing and/or removing diglyceride from an edible oil using an enzyme. The free fatty acids that are formed can be removed by distillation in order to improve the quality of the oil. The document does not deal with PFAD or the recovery of tocols from PFAD but is concerned only with the quality of the refined palm oil.

EP-A-0333472 relates to the production of tocopherols and tocotrienols from PFAD by a process involving the formation of alkyl esters. U.S. Pat. No. 6,159,347 and U.S. Pat. No. 5,487,817 also describe processes for separating tocols that involve the step of esterification.

U.S. Pat. No. 5,512,691 discloses a process for the production of tocopherol concentrates which involves esterification of relatively volatile alcohols followed by distillation.

GB 501,194 discloses the use of antioxidants obtained by distillation for stabilizing oils or fats.

WO 00/15201 describes compositions comprising phytostanols, phytosterols, and tocotrienols for treating cardiovascular disease.

EP-A-1044687 relates to powders containing tocotrienols.

Certain tocotrienol products are known, such as Tocomin 50% from the company Carotech Inc. The analysis of the product from January 2008 indicates a high tocopherol content and a low sterol content.

Black et al, *J Nutr*, 130, 2000, 2420-2426 investigates the effect of vitamin E and beta-carotene on atheroma formation.

Chu et al, *Food Chemistry*, vol 79, no 1, October 2002, 55-59 describes the factors affecting pre-concentration of tocopherols and tocotrienols from PFAD by lipase-catalysed hydrolysis. The lipase used is non-selective and hydrolyses all of the glycerides present.

A process for concentrating sterols in shea oils is disclosed in U.S. Pat. No. 6,399,138. Shea oil and palm oil are unrelated materials having different fatty acid profiles and containing different components. Shea sterols are chemically unrelated to tocols and have distinct physical properties as well as unrelated effects and applications.

There remains a need for a process that can produce tocols from products derived from palm oil, such as palm fatty acid distillate. In particular, there is a need for processes that can produce tocols by processes that are relatively simple and/or cost effective and do not require solvents and harsh reagents that are difficult to handle, such as strong alkalis.

According to the invention in a first aspect, there is provided a process for producing a composition comprising at least 3% by weight of total tocopherols and tocotrienols comprising:

providing a product obtained from palm oil comprising tocopherols and tocotrienols, together with free fatty acids and monoglycerides and diglycerides of fatty acids;

hydrolysing at least part of the monoglycerides and diglycerides with a lipase to form the corresponding free fatty acids;

removing at least part of the free fatty acids after hydrolysis; and recovering a composition comprising a higher level of tocopherols and tocotrienols than are present in the product obtained from palm oil.

In another aspect, the invention provides a composition which comprises from 25 to 50% by weight of total tocopherols and tocotrienols, wherein the weight ratio of tocopherols to tocotrienols is in the range of from 1:2 to 1:4, from 5 to 20% (such as from 5 to 15%) by weight squalene, from 10 to 30% by weight sterols and less than 5% by weight free fatty acids.

In a further aspect, the invention provides a food supplement in the form of a soft gel or a hard capsule comprising an encapsulating material and, encapsulated within the capsule, a composition of the invention.

In yet another aspect, the invention provides a food product comprising a composition of the invention.

Also provided by the invention is a cosmetic formulation comprising a composition of the invention.

Another aspect of the invention is a fat or oil comprising from 5 ppm to 500 ppm of a composition of the invention.

In another aspect, the invention provides the use of a composition of the invention as an antioxidant.

In another aspect, the invention provides a composition of the invention for improving heart health.

In a further aspect, the invention provides a composition of the invention for use in lowering cholesterol.

Also provided by the invention in another aspect is a composition comprising squalene, sterols, tocopherols and tocotrienols, wherein the composition comprises at least 25% by weight of squalene and the weight ratio of squalene to total tocopherols and tocotrienols is at least 1.5:1, preferably at least 2.5:1 and the weight ratio of squalene to sterols is greater than 3:1, preferably greater than 5:1.

The term fatty acid, as used herein, means straight chain carboxylic acids having from 10 to 24 carbon atoms, which may be saturated or may contain one or more (typically from 1 to 3) double bonds. Preferably, the fatty acids are present in palm oil and include palmitic acid and oleic acid as main components (both acids together being present in an amount of greater than 50% by weight based on total fatty acids), together with myristic acid, stearic acid and linoleic acids as relatively minor components.

The invention involves a process for producing a product that is enriched in tocols and other components of palm oil such as squalene. The process can be carried out simply and effectively. The product of the invention is a material that has a high commercial value and can be used in a number of different applications.

The product obtained from palm oil that is used as the starting material for the process of the invention typically comprises tocopherols and tocotrienols in an amount of from 0.5 to 5% by weight, more preferably from 0.8 to 4% by weight, even more preferably from 1 to 3% by weight. Alternatively, or additionally, the product obtained from palm oil preferably comprises monoglycerides and diglycerides in an amount of from 20 to 45% by weight, more preferably from 25 to 42% by weight, even more preferably from 30 to 40% by weight. The product will usually comprise free fatty acids, preferably in an amount of from 20 to 50% by weight, even more preferably from 25 to 45% by weight, such as from 27 to 40% by weight or from 28 to 35% by weight. Preferably, the product obtained from palm oil also comprises triglycerides, more preferably in an amount of from 15 to 40% by weight, more preferably from 18 to 35% by weight, such as from 20 to 30% by weight. The product obtained from palm oil will usually comprise squalene in an amount of from 2 to 4% and sterols in an amount of from 1 to 2%.

The product obtained from palm oil that is used as the starting material for the process of the invention is preferably a palm fatty acid distillate. Palm fatty acid distillates (PFADs) are commercially available from the refining of palm oil and are, for example, available from IOI Bulk Oils Europe. Typically, PFAD is obtained as the volatile fraction following the steam distillation of palm oil at reduced pressure. The residue obtained after distillation is refined palm oil, which principally contains triglycerides. It will be appreciated that the process of the invention may be operated with materials other than PFAD, which are obtained from palm oil and have a similar composition. For example, the invention may be carried out on PFAD that has been further treated, such as chemically or physically, in order to alter its chemical composition.

The process of the invention comprises the step of hydrolysing at least part of the monoglycerides and diglycerides with a lipase to form the corresponding free fatty acids. Monoglycerides are hydrolysed to the free fatty acid and glycerol. Diglycerides are initially hydrolysed to monoglyceride and free fatty acid; the monoglyceride may then be hydrolysed to free fatty acid and glycerol. Suitable lipases (i.e., enzymes having the ability to cleave the acyl bond in mono- and/or diglycerides of the fatty acids, preferably both the mono- and diglycerides), include bacterial and fungal lipases, such as the lipase from *Penicilium camembertii*, sold as Lipase G by Amano Enzymes Inc, Japan. It will be appreciated that the lipase used in the process of the invention is specific for mono- and di-glycerides. Thus, the hydrolysis of triglycerides occurs not at all or only to a small extent relative to the hydrolysis of the mono- and di-glycerides.

Typically, the hydrolysis is carried out in the presence of water. The preferred medium for the hydrolysis step comprises from 10 to 40% by weight of water, more preferably from 20 to 30% by weight of water. The temperature of the hydrolysis is preferably from 20 to 50° C., more preferably from 35 to 45° C. The reaction is preferably carried out until the desired degree of hydrolysis has been achieved, more preferably until the reaction is substantially at equilibrium.

The product of the hydrolysis reaction is preferably treated so as to separate the aqueous fraction (comprising water and glycerol) from the oil phase (containing the tocols, squalene, sterols, free fatty acids, triglycerides and any remaining mono- and/or diglycerides), which is used in the subsequent stages of the process. The oil phase may be dried. The intermediate product that is obtained as the oil phase at this stage of the process typically comprises from 15% to 40% by weight triglycerides.

The hydrolysis converts the mono- and/or di-glycerides to release the corresponding free fatty acids. In a subsequent process step, and optionally after one or more intervening steps such as separation, drying and a degree of purification, the free fatty acids are removed as a distillate by distillation. Preferably, the distillation is carried out at a temperature of from 140 to 170° C. and a pressure of 0.01 to 0.5 mbar. The residue (non-volatile fraction) after distillation preferably comprises tocopherols and tocotrienols in a total amount of from 2 to 6% by weight. The level of free fatty acids is preferably reduced to less than 10% by weight, more preferably less than 5% by weight. This product may be recovered and used as a composition comprising a higher level of tocopherols and tocotrienols. This distillation step may be repeated one or more times to increase the purity of the residue.

In a preferred embodiment, the product obtained as the residue of the distillation to remove free fatty acids is further distilled to produce a composition comprising an even higher level of tocopherols and tocotrienols as a distillate. In this further step, the composition comprising tocols is distilled from the less volatile material at a higher temperature and/or a lower pressure than the previous distillation step. Preferably, this distillation step is carried out at a temperature of from 160 to 210° C. (such as from 180 to 210° C.) and a pressure of from 0.01 to 0.5 mbar. The distillate may be recovered and used as such. The distillate preferably comprises from 10 to 30% by weight free fatty acids (such as from 15 to 25% by weight free fatty acids), from 10 to 25% (such as from 10 to 30%) by weight total tocotrienols and tocopherols (such as from 12 to 20% (or from 23 to 28%) by weight total tocotrienols and tocopherols), together with from 10 to 30% (e.g., from 10 to 20%) by weight squalene and from 5 to 15% by weight sterols. This distillation step may be repeated one or more times to increase the purity of the distillate.

The process of the invention preferably comprises a further step of stripping free fatty acids from the distillate (i.e., removing more of the free fatty acids as a volatile fraction) before recovering the composition comprising a higher level of tocopherols and tocotrienols. The fatty acids are preferably stripped at a temperature of from 140 to 170° C. and a pressure of from 0.01 to 0.5 mbar. Again, this stripping step may be repeated one or more times to increase the purity of the residue.

Preferably, one or more or all of the steps involving distillation or stripping is or are carried out by short path molecular distillation. Suitable apparatus for carrying out the short path molecular distillation of fatty acids and glycerides from palm oil, which is suitable for use in the invention, is commercially available, for example from Pope Scientific Inc, USA and/or UIC GmbH, Germany.

The product obtained in the process comprises greater than 3% by weight total tocopherols and tocotrienols, preferably greater than 10% by weight, more preferably greater than 15% by weight. Typically, the product comprises from 25 to 50% by weight of total tocopherols and tocotrienols, such as from 30 to 40% by weight of total tocopherols and tocotrienols. The weight ratio of tocopherols to tocotrienols in the composition is preferably in the range of from 1:2 to 1:4, more preferably in the range of from 1:2 to 1:3.5. The composition comprising a higher level of tocopherols and tocotrienols preferably comprises from 5 to 20% (such as from 5 to 15%) by weight squalene, such as from 10 to 18%, or from 6 to 10%, by weight squalene. Squalene is a useful commercial product in its own right, having application in cosmetics, for example, and adds value to the composition. The composition preferably comprises from 10 to 30% by weight sterols, such as from 12 to 20% by weight sterols.

The process of the invention, and the product obtained in the invention, are preferably solvent free i.e., no solvents (other than water) are used in the process and, accordingly, no traces of solvent are present in the product.

The invention provides a composition which comprises from 25 to 50% by weight of total tocopherols and tocotrienols, wherein the weight ratio of tocopherols to tocotrienols is in the range of from 1:2 to 1:4, from 5 to 20% (such as from 5 to 15%) by weight squalene, from 10 to 30% by weight sterols and less than 5% by weight free fatty acids. This composition is preferably obtainable directly or indirectly from palm oil.

The composition of the invention preferably contains triglycerides in an amount of from 1% to 20% by weight, such as from 5% to 15% by weight.

The tocotrienols preferably include α-, β-, γ-, and δ-tocotrienols and the tocopherols preferably include α-, β-, γ-, and δ-tocopherols.

The composition of the invention may be used in a number of applications, for example as an anti-oxidant or as a source of Vitamin E.

It has been found that compositions of the invention are surprisingly effective in stabilising fats and oils. Therefore, the invention also provides a fat or oil comprising from 5 ppm to 500 ppm of a composition of the invention, with the composition of the invention preferably being present in an amount of from 25 ppm to 400 ppm, more preferably from 50 ppm to 300 ppm, even more preferably from 100 ppm to 250 ppm. It will be appreciated that ppm values are calculated by weight. The fat or oil comprises fatty acids, usually as triglycerides (typically in an amount of at least 90% by weight of triglycerides based on the weight of the fat or oil).

The composition of the invention may be used as an antioxidant in medical or in non-medical applications. For example, the composition may be used as an antioxidant for improving heart health. The use of the composition preferably involves lowering cholesterol. The composition may also be used as an antioxidant to inhibit or prevent the oxidation of certain oxidisable materials, including foodstuffs.

The composition may be packaged and sold as a food supplement. The food supplement is preferably in the form of a soft gel or a hard capsule comprising an encapsulating material, in which the composition of the invention is encapsulated. The encapsulating material is preferably selected from the group consisting of gelatin, starch, modified starch, and starch derivatives.

The composition of the invention may also be used in a food product, preferably in an amount of from 0.01% to 25% by weight of the food product. Preferred food products are those selected from the group consisting of: fats; oils; margarines; low fat spreads; very low fat spreads; bicontinuous spreads; water continuous spreads; confectionery products, such as chocolates, coatings or fillings; ice creams; ice cream coatings; ice cream inclusions; dressings; mayonnaises; sauces; bakery fats; shortening or cheese; meal replacement products; health bars; muesli bars; drinks; dairy products; low carbohydrate products; low calorie products; soups; cereals and milk shakes. Dressings are typical food products that may contain the compositions of the invention.

Food products preferably comprise a fat or oil selected from: soybean oil; sunflower oil; rape seed oil, cotton seed oil; cocoa butter and cocoa butter equivalents; palm oil and fractions thereof; enzymically made fats; fish oils and fractions thereof; conjugated linoleic acid and enriched isomer mixtures thereof; gamma linoleic acid and enriched mixtures thereof; hardened liquid oils; and mixtures thereof.

Compositions of the invention may improve the viscosity and/or the taste of the food products. Therefore, the invention also provides the use of a composition of the invention to improve the viscosity and/or taste of a food product. Typically, the improvement is relative to a corresponding food product containing a tocopherol/tocotrienol composition.

Another aspect of the invention is a composition comprising squalene, sterols, tocopherols and tocotrienols, wherein the composition comprises at least 25% by weight of squalene and the weight ratio of squalene to total tocopherols and tocotrienols is at least 1.5:1, preferably at least 2.5:1 and the weight ratio of squalene to sterols is greater than 3:1, preferably greater than 5:1. Preferably, the composition comprises from 25% to 80% by weight squalene.

The compositions of the invention, in all of its aspects, may also be used as a cosmetic, or in a cosmetic formulation, preferably for topical use. Typically, the composition of the invention will be present in a cosmetic formulation in an amount of from about 0.01% to about 25% by weight of the cosmetic formulation. The cosmetic formulations preferably comprise one or more of an emulsifier, a surfactant and a perfume, typically in a total amount of from about 1% to about 60% by weight of the cosmetic formulation.

When the process of the invention involves distillation, it may provide one or more distillate fractions other than the distillate that directly or indirectly forms the composition comprising a higher level of tocopherols and tocotrienols. These other distillate fractions are relatively rich in squalene and may be collected and used individually or as a mixture of two or more such fractions. Since the product is derived from one or more distillate fractions, the major component will be free fatty acids. Typically, the product will comprise free fatty acids in an amount of at least 80% by weight and tocols (i.e., total tocotrienols and tocopherols) in an amount below 1% by weight. Thus, in another aspect, the invention provides a composition comprising squalene, free fatty acids (FFA), glycerides (preferably present in an amount of from 1 to 10% by weight), tocopherols and tocotrienols, wherein the composition comprises at least 5% (preferably 5 to 20%, such as 5 to 15%) by weight of squalene, the weight ratio of squalene to total tocopherols and tocotrienols is at least 7:1, preferably at least 10:1, and the FFA content is at least 80% (preferably 80 to 95%, such as 80 to 92%) by weight.

Preferred aspects of the invention are illustrated in the following non-limiting examples, with reference to the following drawings. In the examples and throughout this specification, all percentages, parts and ratios are by weight unless indicated otherwise.

EXAMPLES

General Procedure

The PFAD is treated with a lipase from *Penicilium camembertii* (Lipase G from Amano enzymes) in order to hydrolyse a part of the existing mono- and di-glycerides to form free fatty acids (FFA) and glycerol. This treatment increases the FFA content in the PFAD from about 25-30% by weight to above 50% by weight. The glycerol formed during this reaction is washed out with demineralised water and, after drying, the lipase treated PFAD is subjected to molecular distillation.

Figure 1:
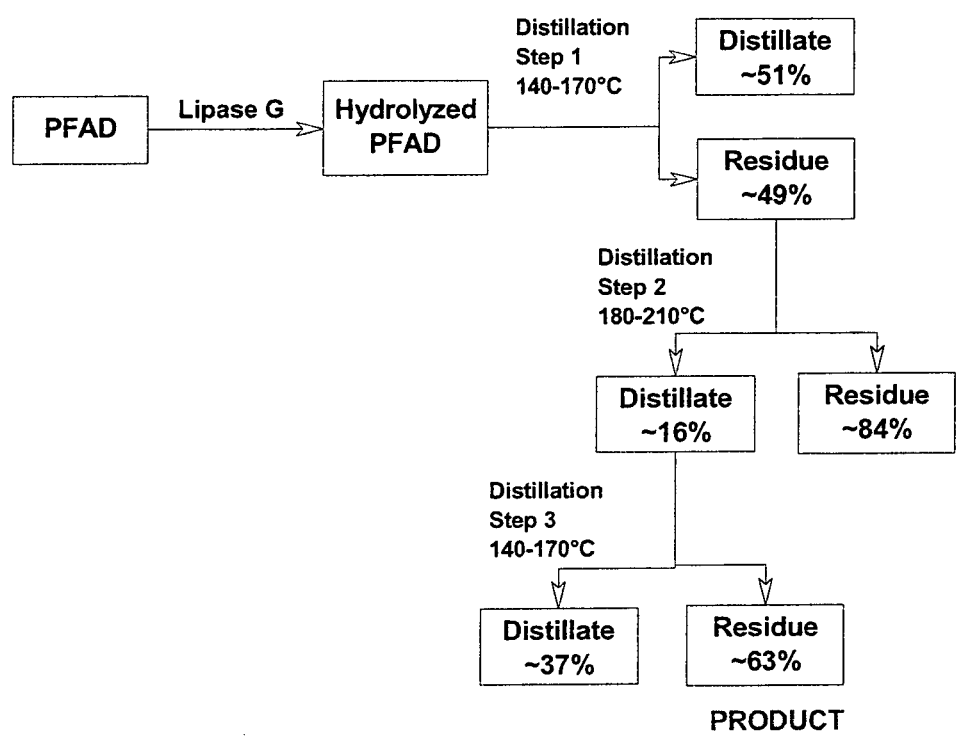
FIG. 1 shows a process scheme in accordance with the present invention.

A counter-current distillation process is used. In the first step the FFA is stripped off at a temperature of 140-170° C. and a pressure of 0.01-0.50 mbar. The residue obtained from the first step is then distilled, in the second step, at a higher temperature of 180-210° C. in order to concentrate the tocols in the distillate. The distillate from the second step still contains a high level of FFA, which is stripped off in an additional distillation step at temperatures of 140-170° C. and a pressure of 0.01-0.5 mbar. The process is illustrated in FIG. 1.

The residue obtained from the third step contains more than 30% by weight total tocols.

This process also produces compounds having more or less the same vapour pressure as the tocopherols and tocotrienols. Therefore, the final product may also contain sterols and/or squalene.

The distillate fractions from the different distillation steps may be combined to obtain a product enriched in squalene, but can also be used as such. Because this product is composed of distillates, the other main part will be free fatty acids, in an amount of at least 80% by weight, while the tocol content will be below 1% by weight.

Example 1

Enrichment of Tocols in PFAD

25% by weight demineralised water was added to about 760 kg of PFAD (containing about 29% by weight of FFA) at a temperature of 39-42° C. Lipase G was added to the reaction mixture in order to start the hydrolysis reaction. The progress of the reaction was monitored by removing samples at regular time intervals and the FFA content was measured by titration. The reaction was stopped when no significant change in FFA content was observed by stirring the mixture at 80° C. for at least 30 minutes. The water phase was drained off and the oil phase was washed once with 15-20% by weight hot demineralised water. After drying, the oil was distilled according to the following conditions:

Step 1—Two-Stage Molecular Distillation

| | |
|---|---|
| Temperature: | 140-170° C. |
| Pressure: | 0.01-0.5 mbar |
| Outlet: | Distillate:Residue = about 51%:49% |

Step 2—Two-Stage Distillation (Feed was the Residue from Step 1)

| | |
|---|---|
| Temperature: | 180-210° C. |
| Pressure: | 0.01-0.5 mbar |
| Outlet: | Distillate:Residue = about 16%:84% |

Step 3—Two-Stage Distillation (Feed was the Distillate from Step 2)

| | |
|---|---|
| Temperature: | 140-170° C.; |
| Pressure: | 0.01-0.5 mbar |
| Outlet: | Distillate:Residue = about 37%:63% |

The composition of the resulting fractions is set out in Table 1.

TABLE 1

Composition of PFAD fractions obtained during the enrichment steps

| | PFAD | Hydrolyzed PFAD | Residue Step 1 | Distillate Step 2 | Residue Step 3 Final product |
|---|---|---|---|---|---|
| FFA [%] | 29.4 | 55.5 | 3.52 | 18.6 | 2.61 |
| T3 + Tph* [%] | 1.94 | 2.00 | 4.61 | 26.63 | 34.13 |
| α-tocopherol | 0.50 | 0.52 | 1.16 | 6.76 | 8.38 |
| β-tocopherol | 0.01 | 0.01 | 0.01 | 0.02 | 0.12 |
| γ-tocopherol | — | — | — | — | — |
| δ-tocopherol | — | — | — | — | — |
| α-tocotrienol | 0.44 | 0.46 | 1.10 | 6.51 | 8.64 |
| β-tocotrienol | 0.06 | 0.06 | 0.12 | 0.64 | 0.85 |
| γ-tocotrienol | 0.68 | 0.68 | 1.66 | 9.60 | 12.34 |
| δ-tocotrienol | 0.25 | 0.27 | 0.56 | 3.10 | 3.80 |
| Sterols [%] | 1.99 | 1.48 | 2.78 | 11.87 | 17.02 |
| Squalene [%] | 3.22 | 3.11 | 2.75 | 15.11 | 8.48 |

*T3 is total tocotrienols and Tph is total tocopherols

Example 2—Comparative Example

A comparative example was carried out using the method described in Example 1 of U.S. Pat. No. 6,399,138.

100% by weight demineralised water was added to about 4 kg of PFAD containing about 25% by weight of FFA at a temperature of 39-42° C. Lipase G was added to the reaction mixture in order to start the hydrolysis reaction. The progress of the reaction was monitored by removing samples at regular time intervals and measuring the FFA content by titration. The reaction was stopped when no significant change in the FFA content was observed by stirring the mixture at 80° C. for at least 30 minutes. The water phase was drained off and the oil phase was washed once with about 50% by weight hot demineralised water. After drying, the oil was distilled according to the following conditions:

One Step Distillation:

| Temperature: | 200° C. |
|---|---|
| Pressure: | 0.5 mbar |
| Feed rate: | 0.4 L/hr |

TABLE 2

Composition of distillate and residue fractions

|  | PFAD | Hydrolyzed PFAD | Residue | Distillate |
|---|---|---|---|---|
| FFA [%] | 25.6 | 45.7 | 0.14 | 92.9 |
| T3 + Tph [%] | 1.97 | 1.97 | 2.21 | 1.64 |
| α-tocopherol | 0.51 | 0.52 | 0.57 | 0.46 |
| β-tocopherol | 0.01 | 0.01 | — | 0.01 |
| γ-tocopherol | — | — | — | — |
| δ-tocopherol | — | — | — | — |
| α-tocotrienol | 0.46 | 0.45 | 0.57 | 0.33 |
| β-tocotrienol | 0.06 | 0.06 | 0.06 | 0.05 |
| γ-tocotrienol | 0.69 | 0.68 | 0.76 | 0.55 |
| δ-tocotrienol | 0.24 | 0.25 | 0.25 | 0.24 |

This process failed to produce a composition having a significantly increased content of total tocotrienols and tocopherols compared to the PFAD starting material.

Example 3

The following is an example of a filled gelatin capsule according to the invention. A composition comprising of the invention is encapsulated into a gelatin capsule according to methods well-known in the art. The resulting encapsulated product contains 500 mg of the composition and one capsule can be taken up to four times daily by an adult human.

Soft gel capsules are produced by rotary die processing. The material for the outside shell of the capsules, the gel, and the fill are formulated separately. Once the gel mass and the fill mass are ready, the gel is spread into thin film to form two gelatin ribbons which are then rolled over two separate dies which determine the size and the shape of the capsules. As the gelatin films adapt to the dies, the fill is carefully dosed to a level of 500 mg oil per capsule and injected between the two gelatin ribbons which are sealed immediately afterwards by applying heat and pressure. Capsules fall from the machine and are then dried under a stream of hot air.

Example 4

The antioxidant activity of a tocotrienol/tocopherol composition of the invention was compared to d-mixed tocopherols with the help of a Rancimat. Both antioxidants were evaluated by their performance to stabilize lard against oxidative deterioration. Lard was selected because of the absence of natural occurring antioxidants. For instance vegetable oils like palm oil contain natural occurring antioxidants which might effect the analysis.

Figure 2:
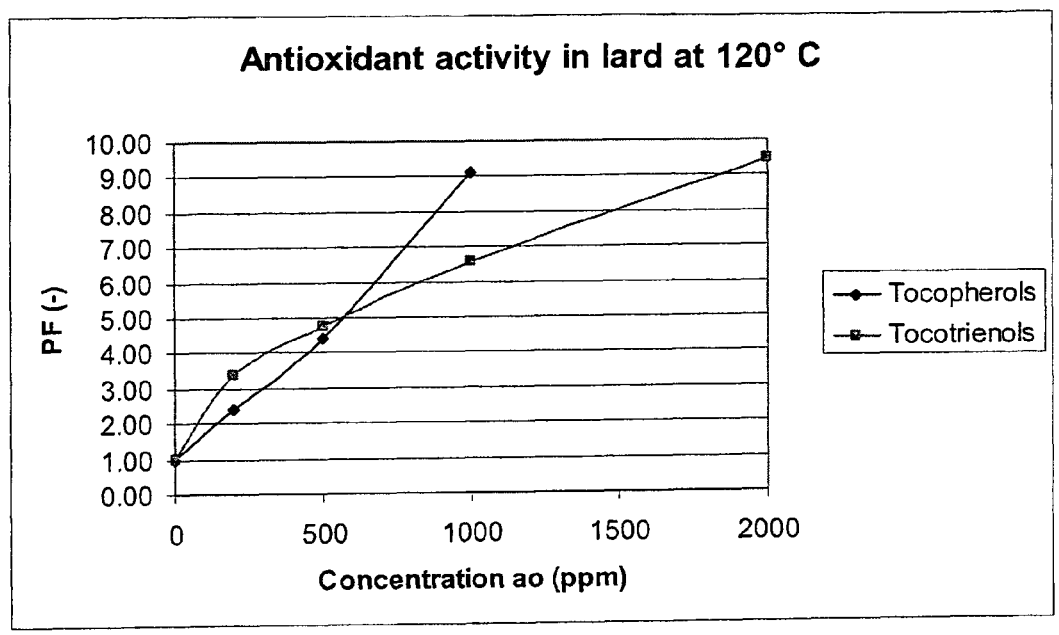
FIG. 2 shows the antioxidant activity of the compositions of the invention in lard.

The d-mixed tocopherols are added by using a commercial blend of tocopherols (Tocoblend L50-IP). The concentration of d-mixed tocopherols and tocotrienols/tocopherols of the invention added to the lard was 200 ppm, 500 ppm, 1000 ppm and 2000 ppm (the latter only for the composition of the invention), based on active material, in order to compare both antioxidants equally. The composition of the invention contained a total of 34.6% of total tocols (25.6% of tocotrienols and 9.0% of tocopherols), the Tocoblend L50-IP (batchnr. 561390) contains 51% of d-mixed tocopherols. The results are shown in the table below and in FIG. 2 (in which the squares ■ represent the composition of the invention and the diamonds ♦ represent the conventional Tocoblend product).

The results are expressed with the use of the protection factor (PF), a widely used parameter for indicating the antioxidant activity of an antioxidant:

PF=IP/IP0, where IP is an induction period of oil with addition of an antioxidant and IP0 is an induction period of oil without the addition of the antioxidant PF>1 indicates an antioxidant activity, a higher PF indicates a higher antioxidant activity. A value of PF=1 corresponds to no antioxidant activity and values of PF<1 mean prooxidative activity.

| Antioxidant | Amount of active ingredient (%) | Amount of antioxidant (ppm) | Amount of active material (ppm) | Average run time, IP (h) | Protection Factor |
|---|---|---|---|---|---|
| Reference | — | — | — | 0.73 | 1 |
| Tocoblend L50-IP | 51% d-mixed tocopherols | 392 | 200 | 1.75 | 2.41 |
| Tocoblend L50-IP | 51% d-mixed tocopherols | 980 | 500 | 3.20 | 4.41 |
| Tocoblend L50-IP | 51% d-mixed tocopherols | 1960 | 1000 | 6.60 | 9.10 |
| Tocotrienolen | 34.6% Tocols | 578 | 200 | 2.45 | 3.38 |
| Tocotrienolen | 34.6% Tocols | 1445 | 500 | 3.45 | 4.76 |
| Tocotrienolen | 34.6% Tocols | 2890 | 1000 | 4.78 | 6.59 |
| Tocotrienolen | 34.6% Tocols | 5780 | 2000 | 6.85 | 9.45 |

At concentrations <500 ppm, the composition of the invention is more effective against oxidation in lard at 120° C. At concentrations >500 ppm d-mixed tocopherols are more effective against oxidation in lard at 120° C. This result means that at the lower concentrations of antioxidant that are typically used to stabilise fats and oils, the composition of the invention is surprisingly more effective than a conventional tocolpherol composition.

Example 5

Figure 3:
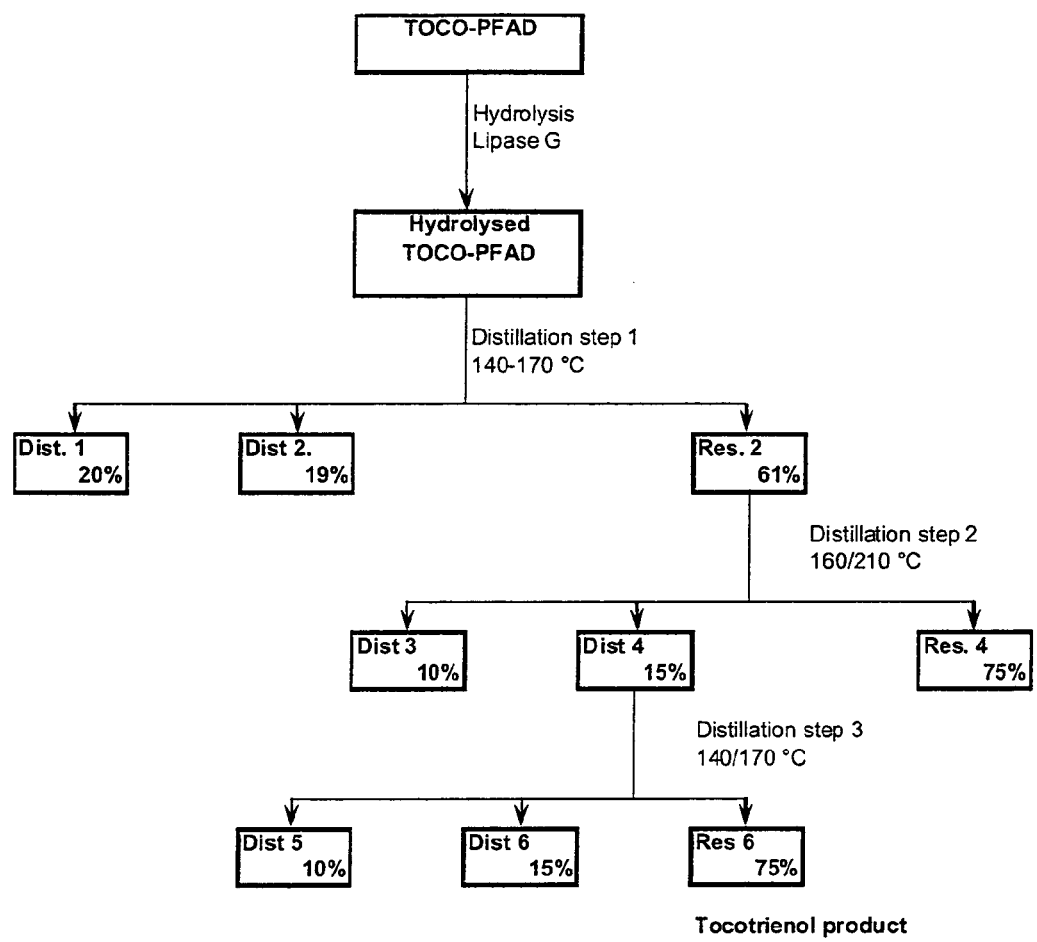
FIG. 3 shows another process scheme in accordance with the invention.

Production of Tocotrienol/tocopherols Composition and Squalene Concentrate from PFAD 25% by weight demineralised water was added to about 485 kg of PFAD (containing about 26.4% by weight of FFA) at a temperature of 39-42° C. Lipase G was added to the reaction mixture in order to start the hydrolysis reaction of diglycerides and monoglycerides present in the reaction mixture. The progress of the reaction was monitored by removing samples at regular time intervals and the FFA content was measured by titration. The reaction was stopped when no significant change in FFA content was observed by stirring the mixture at 80° C. for at least 30 minutes. The water phase was drained off and the oil phase was washed once with 15-20% by weight hot demineralised water. After drying, the oil was distilled according to the following conditions (see FIG. 3, in which "Dist" stands for distillate and "Res" stands for residue):

Step 1—Two-Stage Molecular Distillation

| | |
|---|---|
| Temperature: | 140-170° C. |
| Pressure: | 0.01-0.5 mbar |
| Outlet: | Distillate 1:Distillate 2:Residue 2 = about 20%:19%:61% |

Step 2—Two-Stage Distillation (Feed was the Residue from Step 1)

| | |
|---|---|
| Temperature: | 160-210° C. |
| Pressure: | 0.01-0.5 mbar |
| Outlet: | Distillate 3:Distillate 4:Residue 4 = about 10%:15%:75% |

Step 3—Two-Stage Distillation (Feed was the Distillate 4 from Step 2)

| | |
|---|---|
| Temperature: | 140-170° C.; |
| Pressure: | 0.01-0.5 mbar |
| Outlet: | Distillate 5:Distillate 6:Residue 6 = about 10%:15%:75% |

TABLE 3

Composition of fractions and Tocol concentrate obtained during the enrichment steps

| | PFAD | Hydrolyzed PFAD | Residue Step 1 | Distillate Step 2 | Residue Step 3 Tocol product |
|---|---|---|---|---|---|
| FFA [%] | 26.4 | 47 | 9 | 23 | 2.28 |
| T3 + Tph* [%] | 1.95 | 1.94 | 3.15 | 22.82 | 30.36 |
| α-tocopherol | 0.55 | 0.54 | 0.90 | 6.55 | 8.60 |
| β-tocopherol | 0.01 | 0.01 | 0.01 | 0.34 | 0.71 |
| γ-tocopherol | — | — | — | — | — |
| δ-tocopherol | — | — | — | — | — |
| α-tocotrienol | 0.49 | 0.48 | 0.81 | 4.90 | 6.78 |
| β-tocotrienol | 0.05 | 0.06 | 0.07 | 0.85 | 1.03 |
| γ-tocotrienol | 0.64 | 0.64 | 1.02 | 7.25 | 9.89 |
| δ-tocotrienol | 0.21 | 0.21 | 0.33 | 2.93 | 3.35 |
| Sterols [%] | 1.5 | 1.4 | 1.9 | 4.5 | 11.9 |
| Squalene [%] | 2.1 | 2.3 | 2.5 | 28.1 | 16.9 |

TABLE 4

Composition of different distillate fractions obtained during the enrichment steps that can be used as feedstock for a squalene product

| | Distillate 2 | Distillate 3 | Distillate 5 | Distillate 6 |
|---|---|---|---|---|
| FFA [%] | 99 | 97 | 78 | 58 |
| Squalene [%] | 1.6 | 5.9 | 12.1 | 23.8 |
| Tocols [%] | 0.34 | 0.89 | 0.85 | 2.51 |

TABLE 5

Composition of a possible squalene product that can be obtained from this process

| | Squalene concentrate |
|---|---|
| FFA [%] | 88 |
| Squalene [%] | 6.9 |
| Tocols [%] | 0.68 |
| Glycerides | 4.4 |

Example 6

Three batches of salad dressing were prepared having the following compositions.

Recipe 1: Salad Dressing Comprising Tocotrienol/Tocopherol Composition According to the Present Invention

| | |
|---|---|
| 20.0 | Sunflower oil without added antioxidants |
| 10.0 | Buttermilk |
| 5.0 | Vinegar |
| 2.0 | Sugar |
| 2.0 | Salt |
| 3.0 | Egg yolk |
| 0.5 | Xanthan gum Grinsted-80 ® (Danisco) |
| 0.3 | Garlic dried |
| 0.2 | Onion dried |
| 0.2 | Pepper |
| 0.2 | Lactic acid (80% solution) |
| 0.05 | Parsley dried |
| 0.0289 | Tocotrienols blend (=0.05% tocotrienols on fat-base) |
| 56.53 | Water till 100% |

Recipe 2: Comparative Example: Salad Dressing Comprising Mixture of Tocopherols

| | |
|---|---|
| 20.0 | Sunflower oil without added antioxidants |
| 10.0 | Buttermilk |
| 5.0 | Vinegar |
| 2.0 | Sugar |
| 2.0 | Salt |
| 3.0 | Egg yolk |
| 0.5 | Xanthan gum Grinsted-80 ® (Danisco) |
| 0.3 | Garlic dried |
| 0.2 | Onion dried |
| 0.2 | Pepper |
| 0.2 | Lactic acid (80% solution) |
| 0.05 | Parsley dried |
| 0.0192 | Tocoblend L50 (=0.05% tocopherols on fat-base) |
| 56.53 | Water till 100% |

Recipe 3: Comparative Example: Tocotrienol Composition

| | |
|---|---|
| 20.0 | Sunflower oil without added antioxidants |
| 10.0 | Buttermilk |
| 5.0 | Vinegar |
| 2.0 | Sugar |
| 2.0 | Salt |
| 3.0 | Egg yolk |
| 0.5 | Xanthan gum Grinsted-80 ® (Danisco) |
| 0.3 | Garlic dried |
| 0.2 | Onion dried |
| 0.2 | Pepper |
| 0.2 | Lactic acid (80% solution) |
| 0.05 | Parsley dried |
| 0.0192 | Tocomin 50% from Carotech (=0.05% tocotrienols on fat-base) |
| 56.53 | Water till 100% |

Used Ingredients:
- Sunflower oil POV 0.49, Jan Dekker, batch 67110
- Buttermilk, Friesche Vlag
- Vinegar, Markant huismerk
- Sugar, salt, eggs from supermarket
- Xanthan gum Grinsted-80, Danisco, lotnr. 4450275951
- Spices, Verstegen "spices and sauces"
- White pepper, Cook Cook, batch 5143130
- Lactic acid 80% solution, Purac, batch 0503002427
- Tocotrienols blend, batch LN-DP0001, PR-20070917-004
- Tocoblend L-50 IP, batch 561390 from Vitablend B.V.
- Tocomin 50%, Carotech, batch B6124_1_300108

All salad dressings were prepared according to the following process:

The anti-oxidant mixture was dissolved in the vegetable oil. Sugar, salt and the egg yolk were mixed and then dissolved in warm water of approximately 60° C. A 10% dispersion of xanthan gum in part of the vegetable oil was prepared and slowly added to the above mentioned water phase. Buttermilk and the remaining vegetable oil were added to the reaction mixture. The vinegar and the lactic acid was added and homogenized at 200/50 bar. Finally, the herbs and spices were added and the salad dressing stored at 7° C. for one day.

A trained taste panel evaluated the salad dressings in relation to appearance, smell and taste.

Appearance:

|  | Colour | Viscosity | Stickiness |
| --- | --- | --- | --- |
| Tocotrienol/tocopherols composition according to invention | white | viscous | not sticky |
| Tocoblend L-50 IP | light yellow | unacceptably viscous | sticky |
| Tocomin 50% | yellow | viscous | sticky |

The dressing prepared with Tocomin 50% is much more yellow in colour then the other dressings. The dressing with Tocoblend L-50 and Tocomin 50% are stickier. The dressing with Tocomin 50% is thinner than the other dressings. The dressing containing Tocoblend L-50 is the most viscous compared to the other dressings.

There were no differences in smell. In terms of taste, the dressing with Tocomin 50% was more sour/less spicy than the other dressings.

Results pH:

| Dressings comprising: | pH |
| --- | --- |
| Tocotrienol/tocopherol composition according to invention | 3.50 |
| Tocomin 50% | 3.42 |
| Tocoblend L-50 | 3.51 |

Results Viscosity Measurements:

| Dressings comprising: | 30 seconds | 60 seconds | 90 seconds |
| --- | --- | --- | --- |
| Tocotrienols/tocopherols composition according to invention | 1736 cP/43.2% | 1760 cP/44% | 1768 cP/44.1% |
| Tocomin 50% | 1850 cP/45.8% | 1808 cP/45.6% | 2020 cP/48.1% |
| Tocoblend L-50 | 2459 cP/61.6% | 2451 cP/61.5% | 2475 cP/61.5% |

The salad dressing comprising Tocoblend L-50 IP shows the highest viscosity.

Note:
Temperature dressings = 7.5° C.
Used spindle = no. 63
Speed = 30 rpm
Measured parameters: viscosity in cP and Torque in %

The results show that the dressing comprising the composition of the invention has the best combination of taste, colour, texture and viscosity.

The invention claimed is:

1. Process for producing a composition comprising at least 3% by weight of total tocopherols and tocotrienols comprising:
   providing a product obtained from palm oil comprising tocopherols and tocotrienols, together with free fatty acids and monoglycerides and diglycerides of fatty acids;
   hydrolysing at least part of the monoglycerides and diglycerides with a lipase that is specific for monoglycerides and diglycerides to form the corresponding free fatty acids;
   removing at least part of the free fatty acids after hydrolysis; and
   recovering a composition comprising a higher level of tocopherols and tocotrienols than are present in the product obtained from palm oil.

2. Process as claimed in claim 1, wherein the product of the hydrolysis reaction is treated so as to separate an aqueous fraction comprising water and glycerol from an oil phase containing tocotrienols and tocopherols, squalene, sterols, free fatty acids, triglycerides and any remaining mono- and/or diglycerides.

3. Process as claimed in claim 1, wherein the lipase is from *Penicilium camembertii*.

4. Process as claimed in claim 1, wherein the product obtained from palm oil is a palm fatty acid distillate.

5. Process as claimed in claim 1, wherein the product obtained from palm oil comprises tocopherols and tocotrienols in an amount of from 1 to 5% by weight.

6. Process as claimed in claim 1, wherein the product obtained from palm oil comprises monoglycerides and diglycerides in an amount of from 20 to 45% by weight.

7. Process as claimed in claim 1, wherein the product obtained from palm oil comprises free fatty acids in an amount of from 20 to 50% by weight.

8. Process as claimed in claim 1, wherein the product obtained from palm oil comprises triglycerides in an amount of from 15 to 40% by weight.

9. Process as claimed in claim 1, wherein the hydrolysis is carried out in the presence of water.

10. Process as claimed in claim 1, wherein the free fatty acids are removed as a distillate by distillation.

11. Process as claimed in claim 10, wherein the distillation is carried out at a temperature of from 140 to 170° C. and a pressure of 0.01 to 0.5 mbar.

12. Process as claimed in claim 1, wherein the composition comprising a higher level of tocopherols and tocotrienols is recovered as a distillate.

13. Process as claimed in claim 12, wherein the distillation to form the composition comprising a higher level of tocopherols and tocotrienols is carried out at a temperature of from 160 to 210° C. and a pressure of 0.01 to 0.5 mbar.

14. Process as claimed in claim 13, which comprises a further step of stripping free fatty acids from the distillate before recovering the composition comprising a higher level of tocopherols and tocotrienols.

15. Process as claimed in claim 14, wherein in the further step the fatty acids are stripped at a temperature of from 140 to 170° C. and a pressure of 0.01 to 0.5 mbar.

16. Process as claimed in claim 1, wherein the composition comprising a higher level of tocopherols and tocotrienols comprises from 25 to 50% by weight of total tocopherols and tocotrienols.

17. Process as claimed in claim 16, wherein the weight ratio of tocopherols to tocotrienols in the composition comprising a higher level of tocopherols and tocotrienols is in the range of from 1:2 to 1:4.

18. Process as claimed in claim 1, wherein the composition comprising a higher level of tocopherols and tocotrienols comprises from 5 to 20% by weight squalene.

19. Process as claimed in claim 1, wherein the composition comprising a higher level of tocopherols and tocotrienols comprises from 10 to 30% by weight sterols.

20. Process as claimed in claim 1, wherein the composition comprises from 25 to 50% by weight of total tocopherols and tocotrienols, wherein the weight ratio of tocopherols to tocotrienols is in the range of from 1:2 to 1:4, from 5 to 20% by weight squalene, from 10 to 30% by weight sterols and less than 5% by weight free fatty acids.

21. Process as claimed in claim 1, wherein the process does not comprise the use of alkalis.

22. Process as claimed in claim 1, wherein the composition comprises at least 10% by weight of total tocopherols and tocotrienols.

23. Process for producing a composition comprising at least 3% by weight of total tocopherols and tocotrienols comprising:
   providing a product obtained from palm oil comprising tocopherols and tocotrienols, together with free fatty acids and monoglycerides and diglycerides of fatty acids;
   hydrolysing at least part of the monoglycerides and diglycerides with a lipase that is specific for monoglycerides and diglycerides to form the corresponding free fatty acids;
   removing at least part of the free fatty acids after hydrolysis; and
   recovering a composition comprising a higher level of tocopherols and tocotrienols than are present in the product obtained from palm oil, and 1 to 20% by weight triglycerides.

* * * * *